(12) United States Patent
Roy

(10) Patent No.: US 6,400,146 B1
(45) Date of Patent: Jun. 4, 2002

(54) SENSOR HEAD FOR ACFM BASED CRACK DETECTION

(75) Inventor: George Roy, Manotick (CA)

(73) Assignee: Her Majesty the Queen in right of Canada as represented by the Ministry of Natural Resources, Ottawa (CA)

( * ) Notice: Subject to any disclaimer, the term of this patent is extended or adjusted under 35 U.S.C. 154(b) by 0 days.

(21) Appl. No.: 09/660,178

(22) Filed: Sep. 12, 2000

(51) Int. Cl.[7] .......................... G01N 27/82; G01R 33/12
(52) U.S. Cl. ...................................... 324/242; 324/238
(58) Field of Search .................................. 324/239, 240, 324/242, 243, 232, 226, 262, 238, 529

(56) References Cited

U.S. PATENT DOCUMENTS

| | | |
|---|---|---|
| 3,625,776 A | 12/1971 | Henry |
| 3,670,239 A | 6/1972 | Shiraiwa et al. |
| 3,855,530 A | 12/1974 | Fuji et al. |
| 4,016,487 A | 4/1977 | Neumaier |
| 4,041,379 A | 8/1977 | Karlsson |
| 4,095,181 A | 6/1978 | Harris et al. |
| 4,136,067 A | 1/1979 | Reed et al. |
| 4,271,393 A | 6/1981 | Hansen et al. |
| 4,379,261 A | 4/1983 | Lakin |
| 4,445,089 A | 4/1984 | Harrison |
| 4,480,225 A | 10/1984 | Nance et al. |
| 4,481,471 A | 11/1984 | Miller et al. |
| 4,644,272 A | 2/1987 | Janos |
| 4,673,879 A | 6/1987 | Harris et al. |
| 4,675,605 A | 6/1987 | Watjen |
| 4,799,010 A | 1/1989 | Muller |
| 4,906,927 A | 3/1990 | Urata et al. |
| 5,041,786 A | 8/1991 | Takaishi et al. |
| 5,053,705 A | 10/1991 | Herko |
| 5,130,652 A | 7/1992 | Kawakami et al. |
| 5,258,708 A | * 11/1993 | Sadeghi et al. ............. 324/240 |
| 5,418,459 A | 5/1995 | You et al. |
| 5,432,444 A | 7/1995 | Yasohama et al. |
| 5,461,313 A | 10/1995 | Bohon et al. |
| 5,548,214 A | 8/1996 | Yasohama et al. |
| 5,565,773 A | 10/1996 | Inaguma et al. |
| 5,574,376 A | * 11/1996 | Topp et al. ................. 324/529 |
| 5,589,772 A | 12/1996 | Kugai |
| 5,602,474 A | 2/1997 | Morrey, Jr. |
| 5,648,721 A | 7/1997 | Wincheski et al. |
| 5,729,135 A | 3/1998 | Kugai |
| 5,751,144 A | 5/1998 | Weischedel |
| 5,777,469 A | 7/1998 | Hockey et al. |

FOREIGN PATENT DOCUMENTS

| | | |
|---|---|---|
| EP | 0 566 624 | 12/1996 |
| GB | 2 201 965 | 9/1988 |
| GB | 2 224 575 | 5/1990 |
| GB | 2 286 678 | 8/1995 |

OTHER PUBLICATIONS

Raine, "An Alternative Method For Future Inspection"; DSNDT Journal, Jan./Feb. 1998/ pp 7–16.

* cited by examiner

Primary Examiner—Edward Lefkowitz
Assistant Examiner—Subhash Zaveri
(74) Attorney, Agent, or Firm—Robert A. Wilkes; Robert G. Hendry; Harold C. Baker

(57) ABSTRACT

A sensor head with multiple sensors for ACFM based crack detection and sizing. An alternating current electromagnetic yoke is used to induce a uniform magnetic field on the surface of the test piece. A reference coil in the sensor head detects the background field strength of the magnetic field. Multiple sensors, the axis of each of which is in an angled relationship to the reference coil, detect variations in the magnetic field. The sensor coil axes can be chosen to detect and size both angled and straight cracks.

14 Claims, 4 Drawing Sheets

SENSOR HEAD FOR ACFM BASED CRACK DETECTION

FIELD OF INVENTION

This invention relates to the detection and sizing of cracks in metals using alternating current field measurement methods, and more specifically, to a sensor head and equipment to be used with such methods.

DESCRIPTION OF THE RELATED PRIOR ART

Alternating Current Field Measurement (ACFM) techniques for non-destructive testing are well-known in the industrial world. They have been extensively used in detecting cracks in metals located in inaccessible places such as underneath the sea. They have also been used to detect minute cracks in components such as aircraft skins, pipe surfaces, and the like. However, while the ACFM technique works well, there are some drawbacks with the equipment currently used in applying the techniques. To explain these drawbacks, an explanation of the ACFM technique is required.

The ACFM technique is an electromagnetic non-contacting technique which was developed to detect and size surface breaking defects occurring in different materials and through coatings of various thicknesses. The technique is based on the principle that a current induced in a material produces a magnetic field. Disturbances or singularities in the material cause variances in an otherwise relatively uniform magnetic field. By detecting and measuring these magnetic field variances, defects in the material can be found. Using ACFM, sensors are used to measure the magnetic field above the test area and thereby to detect defects. However, sensors currently being used in ACFM based equipment can only detect and size a specific type of crack. These sensors can detect and size cracks, such as stress or corrosion cracks, in test materials. However, while they can detect slanted cracks, these sensors cannot size slanted cracks nor can they determine the angle of inclination of these cracks. In this context, a straight crack is a crack that is substantially perpendicular to the surface of the material. A slanted crack is a crack that is at an angle to the surface of the material.

One such sensor is that disclosed by Topp and Lugg in EP Application 0 566 624 filed Jan. 10, 1992. In this application, the sensor is comprised of two coils at right angles whose axes intersect at a common central point. As noted above, this sensor arrangement can only detect and size straight cracks.

Accordingly, there is a requirement for a sensor arrangement and equipment which can be used with ACFM techniques to detect and size all types and configurations of cracks.

SUMMARY OF THE INVENTION

The present invention seeks to provide a sensor head in which multiple sensors are arranged to detect and size slanted cracks by detecting different components of variations in the magnetic field produced by the alternating current. A yoke is used to induce a uniform alternating current in the test material. A reference coil detects the background field strength of the magnetic field in the horizontal direction. The multiple sensor coils, the axis of each of which is in an angled relationship with the reference coil axis, detects variations in the magnetic field in the vertical plane at different angles. One of the sensor coils can be perpendicular to both the yoke axis and the reference coil axis and can detect and size straight cracks. Other sensor coils, having axes angled away from this first sensor coil, can detect and size angled cracks.

In a first embodiment, the present invention provides a sensor head for detecting variations in a magnetic field induced on the surface of a test piece by an electromagnetic elongated yoke, the sensor head comprising
  a reference coil for sensing magnetic fields produced by the current, the reference coil having a longitudinal axis parallel to a longitudinal axis of the elongated yoke, and the reference coil being disposed between the yoke and the test piece;
  a plurality of sensor coils for sensing variations in magnetic fields, each sensor coil having a longitudinal axis which intersects the longitudinal axis of the reference coil and each sensor coil being positioned between the reference coil and the yoke; and
  mounting means for mounting the reference coil and the plurality of sensor coils in the sensor head.

In a second embodiment, the present invention provides an ACFM testing module for testing a test piece, the module comprising:
  an electromagnetic elongated yoke;
  a reference coil having a longitudinal axis parallel to a longitudinal axis of the yoke, the reference coil being disposed between the yoke and the test piece;
  a plurality of sensor coils, each sensor coil having a longitudinal axis which intersects the longitudinal axis of the reference coil and each sensor coil being positioned between the reference coil and the yoke;
  power supply means providing electrical power to the yoke;
  measurement means, the measurement means being coupled separately to the reference coil and to each sensor coil; and
  mounting means for mounting the reference coil and the plurality of sensor coils in a sensor head.

In a third embodiment, the present invention provides a sensor head for use with ACFM crack detection and sizing and for use with an electromagnetic elongated yoke inducing a current sheet in a test piece, the head comprising:
  a reference coil having a longitudinal axis parallel to a longitudinal axis of the yoke, the reference coil being positioned between the test piece and the yoke;
  at least three sensor coils, each sensor coil having a longitudinal axis which is perpendicular to the longitudinal axis of the reference coil, each sensor coil being positioned between the reference coil and the yoke; and
  mounting means for mounting the reference coil and the at least three sensor coils in the sensor head;
  wherein the longitudinal axes of the at least three sensor coils are located in a plane perpendicular to the longitudinal axis of the reference coil.

In a fourth embodiment, the invention provides a method of detecting and sizing defects in or near to a surface of a test piece, said method comprising:
  a) energizing a yoke to induce a uniform alternating current on the surface of the test piece;

b) positioning a reference coil such that a longitudinal axis of the reference coil is parallel to a longitudinal axis of the yoke;

c) positioning at least two sensor coils with their axes at an angle to the reference coil axis;

d) moving a sensor head including the reference coil, the sensor coils and the yoke across the surface of the test piece;

e) detecting variations in electromotive force induced in the reference coil f) measuring the variations detected in step e);

g) detecting variations in electromotive force induced in the sensor coils;

h) measuring the variations detected in step g); and i) processing data obtained in steps f) and h) to determine the presence and the size of a defect.

BRIEF DESCRIPTION OF THE DRAWINGS

The invention will now be described, with reference to the following drawings in which.

DETAILED DESCRIPTION OF THE INVENTION

Figure 1:
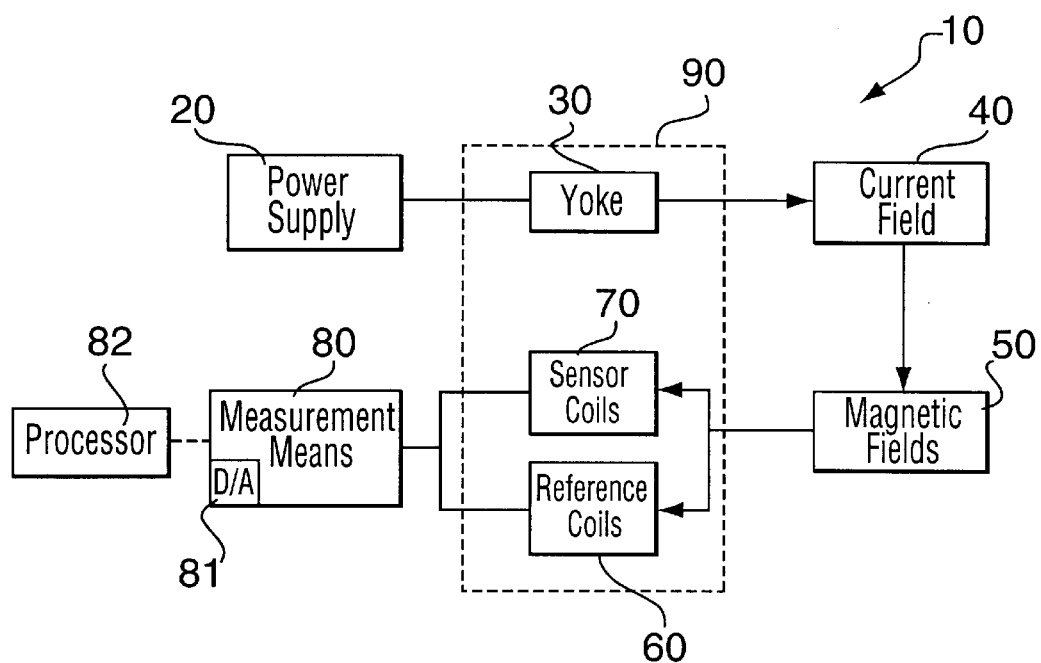
FIG. 1 is a block diagram of a module for ACFM crack detection.

Referring to FIG. 1, a block diagram is shown of a module 10 for ACFM based crack detection and sizing. An alternating current power supply means 20 is coupled to a winding on the yoke device 30. The yoke device 30 induces a current field 40 which, in turn produces, either directly or indirectly, a number of magnetic fields 50. These magnetic fields 50 and the variations in them are detected by both a reference coil 60 and a plurality of sensor coils in the sensor coil assembly 70. The variations are measured by a measurement means 80 such as a voltmeter for measuring small voltages. The yoke 30, the sensor coil assembly 70 and the reference coil 60 are combined in a single sensor head 90. The module 10 is used by first arranging, if possible, the sensor coil assembly 70 to obtain the best reading of the expected magnetic fields. The yoke 10 is then energized to induce the current field 40, and the associated magnetic fields 50. To measure these magnetic fields and their variations, the sensor head 90 is moved across the surface of the test piece 100. The sensor coil assembly 70 and the reference coil 60 then generate a voltage in response to any variations in the magnetic fields caused by a surface defect, such as a crack. These voltage variations are retrieved by the data acquisition means 81 in the measurement means 80, and then transferred to the data processing means 82 for conversion into a crack topography map in a desired format. By measuring these voltage variations, the location, size, depth, and orientation of the crack can be obtained.

Experiments have been successfully conducted using a Keithley (TM) multimeter 2010 as the measurement means with the multimeter having a precision of 100 nV. The power supply means provided the yoke with 5 kHz, 10 A, 0.2 V AC current.

Figure 2:
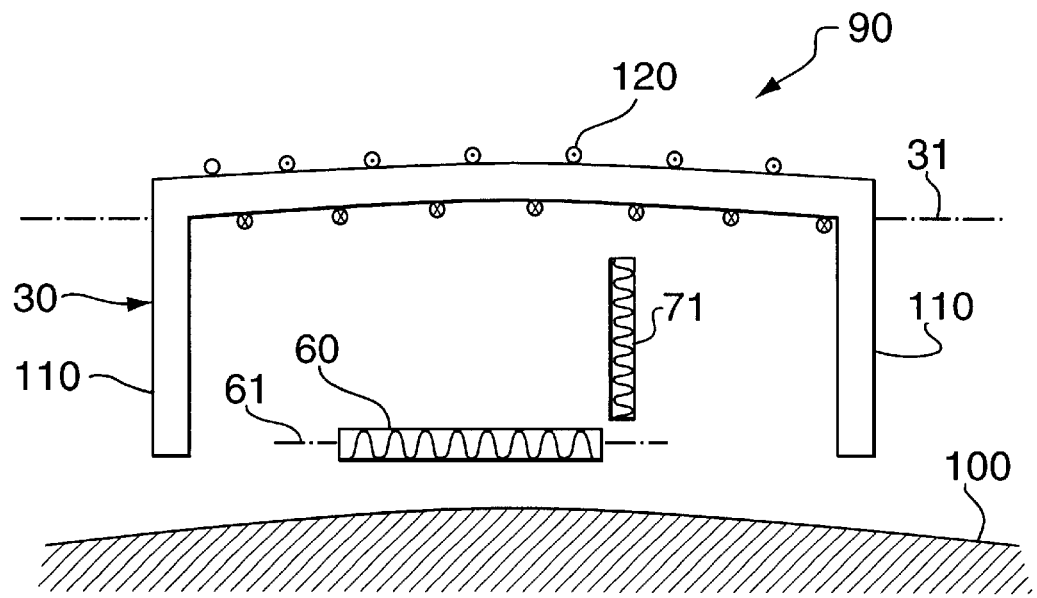
FIG. 2 is a side view of a sensor head to be used with the module in FIG. 1.
Figure 3:
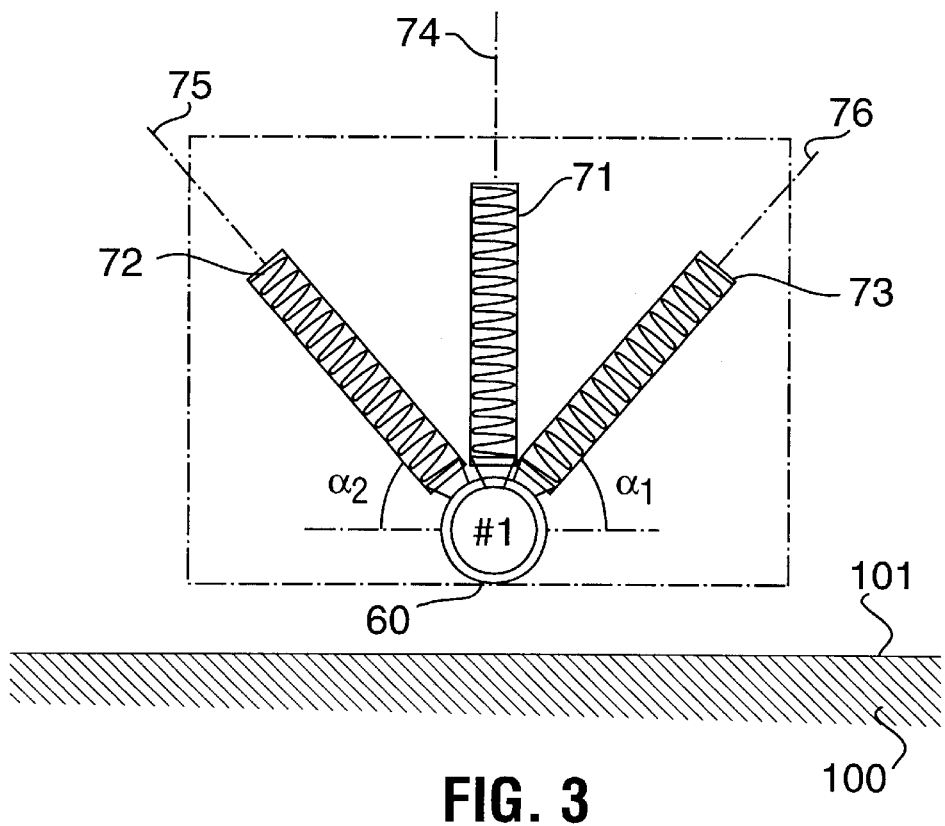
FIG. 3 is an end view of a sensor coil configuration.

A configuration for a sensor head 90 is shown in FIGS. 2 and 3. The axis 61 of the reference coil 60 must be parallel to the axis 31 of the yoke 30 so that the reference coil 60 can provide a signal indicative of the background magnetic field strength in the horizontal direction. The yoke 30 is a ferromagnetic strip with two angled ends 110. Wrapped around the yoke 30 are sufficient turns 120 of copper wire to provide a suitable field strength on the surface of the test piece.

The reference coil 60, and the sensor coils in the sensor coil assembly 70 are each essentially a coil of wire wrapped around a suitable form to provide a generally circular cross-section. While an air-core coil is preferable, other types of coils are acceptable as long as these coils are capable of responding to small magnitude magnetic fields. Experiments have shown that multiple turns of very fine wire around a small paper core is acceptable.

In one setup, the yoke 30 utilized a ferritic core with 44 turns of 20 AWG gauge wire in a single layer. The yoke was 44 mm in length, 32 mm in width, and had a height of 3 mm. The reference coil 60 was an air core centered coil having 4 layers of wire with each layer having 30 turns of 38 AWG gauge wire. The reference coil was approximately 8 mm long and had a diameter of 3 mm.

In the same setup, each sensor coil was also an air core centered coil with 4 layers of wire. Each layer had 50 turns of 38 AWG gauge wire with each coil being approximately 4 mm in length and having a diameter of about 2 mm.

Figure 4:
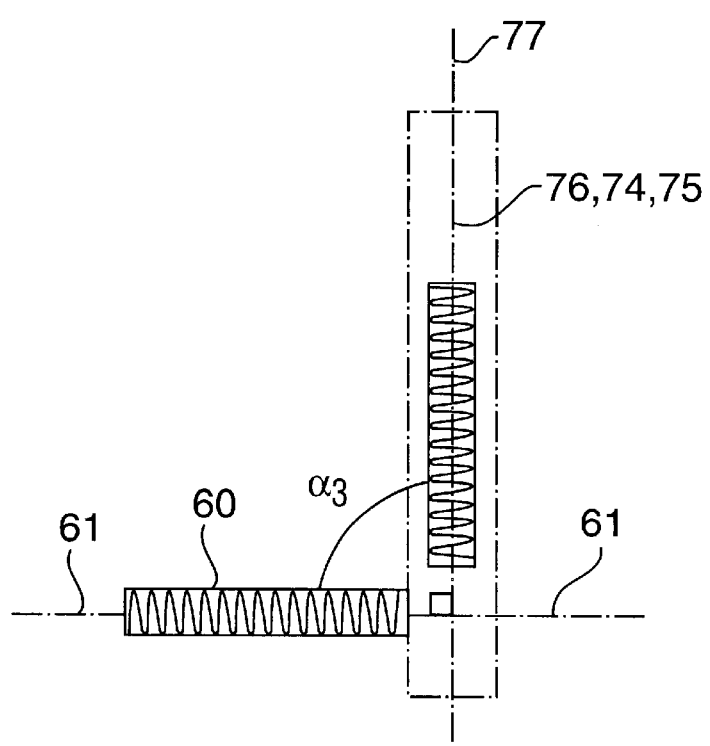
FIG. 4 is a side view of the configuration illustrated in FIG. 3.

General configurations of the reference coil 60 and the sensor coils in the sensor coil assembly 70 can take many forms. A preferable embodiment, shown as an end view in FIG. 3 and in side view in FIG. 4, illustrates three sensor coils 71, 72, 73 with a first sensor coil 71 being perpendicular to the reference coil 60. For ease of reference, the longitudinal axes of the sensor coils 71, 72, 73 and of the reference coil 60 will be used to define their positioning and placement.

FIG. 3 shows that the longitudinal axes 74, 75, 76 of the sensor coils 71, 72, 73 respectively are perpendicular to the longitudinal axis 61 of the reference coil 60; in FIG. 3 the longitudinal axis 61 of the reference coil 60 is perpendicular to the plane of the paper. FIG. 4 shows that the axes 74, 75, 76 of the sensor coils 70, 71, 72 are all contained in a plane 77 which is perpendicular to the longitudinal axis 61 of the reference coil 60. FIG. 3 also shows that the sensor coils 71, 72, 73 are generally symmetrical relative to the axis 74.

Figure 5:
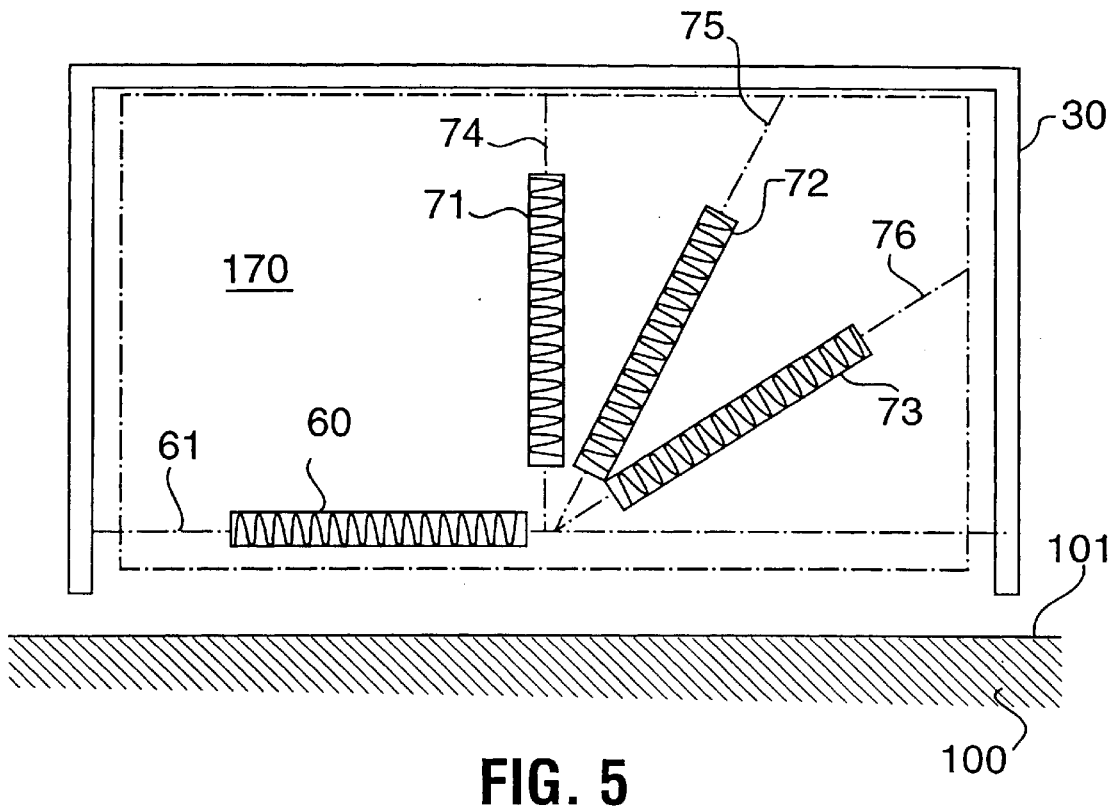
FIG. 5 is a side view of another configuration of sensor coils in a sensor head.
Figure 6:
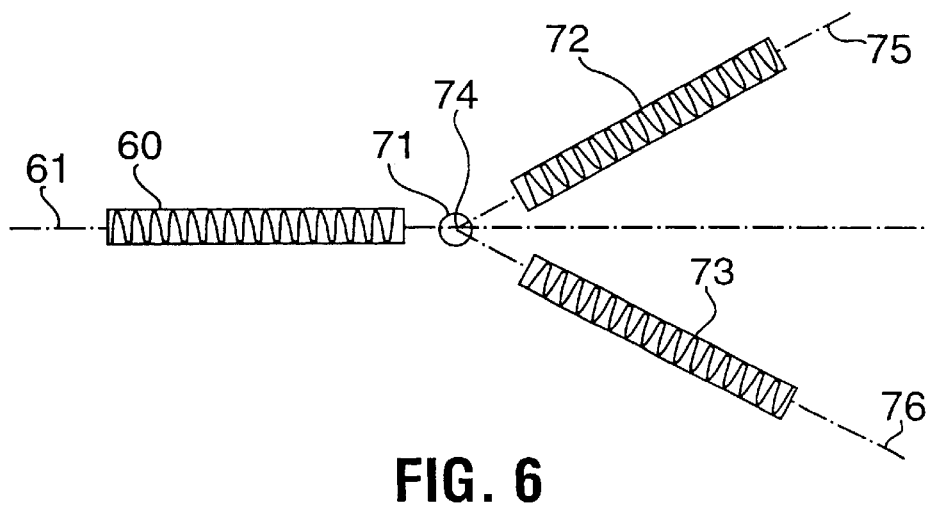
FIG. 6 is a top view of the sensor coil configuration illustrated in FIG. 5.

While the configuration in FIGS. 3 and 4 are preferable, other configurations are also possible. FIG. 5 and FIG. 6 show other configurations with three sensor coils 71, 72, 73. FIG. 5 shows a side view and FIG. 6 shows a plan view. As can be seen from FIGS. 5 and 6, the longitudinal axes 74, 75, 76 of the sensor coils 70, 71, 72 intersect the longitudinal axis 61 of the reference coil 60.

Figure 7:
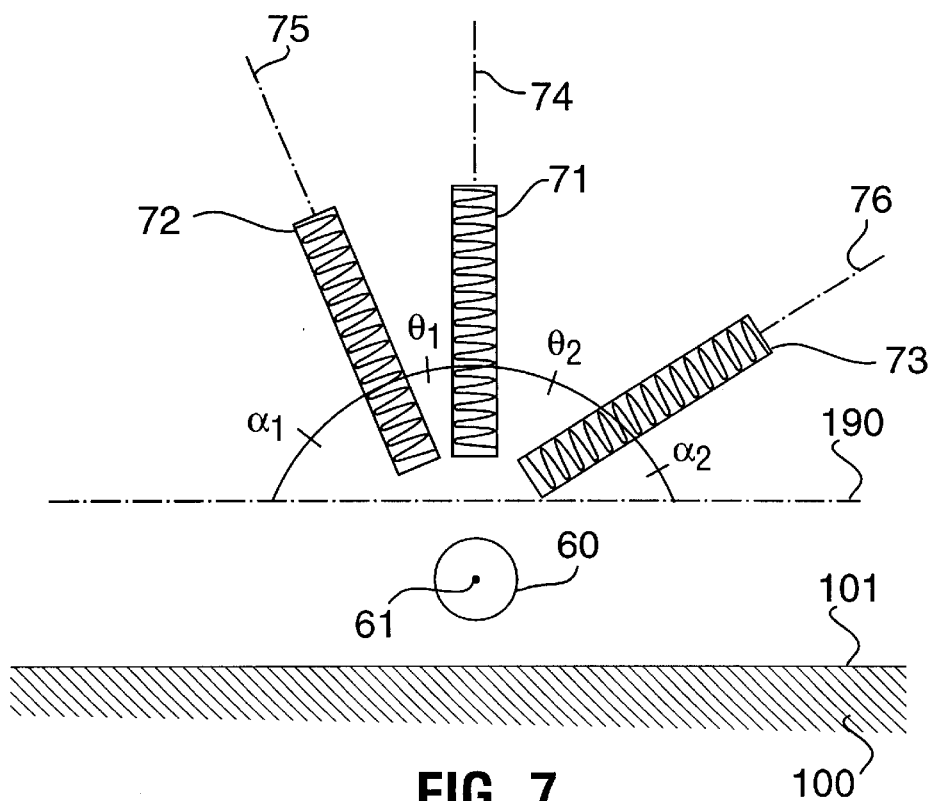
FIG. 7 is an end view of another embodiment of the sensor coil configuration shown in FIG. 3.

FIG. 7 shows an alternative arrangement of the sensor coil configuration of FIG. 3. In FIG. 7 the angles $\theta_1$ and $\theta_2$ between the axes of the sensor coils 71, 72, and 73 are not equal. Even when $\theta_1$ and $\theta_2$ are the same, it is not necessary that the angles $\alpha_1$ and $\alpha_2$, between the axes of the coils 72, 73 and the line 190 parallel to the surface 100 of the test piece, are the same. These angles are chosen to optimize the signals derived from the sensor coils 72, 73, 74.

Figure 8:
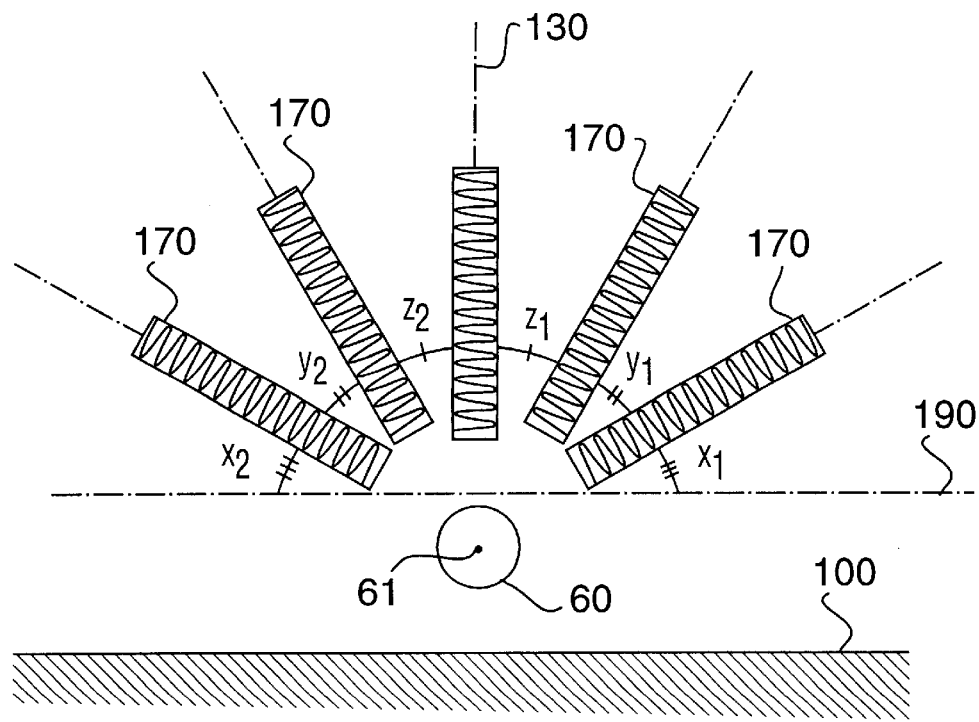
FIG. 8 is an end view of a five sensor coil configuration.

FIG. 8 illustrates one embodiment with five sensor coils 170; this configuration is symmetrical so that each pair of angles $x_1$, $x_2$, $y_1$, $y_2$, $z_1$ and $z_2$ are equal. It is contemplated that at least one of these pairs may not be equal.

While the above configurations are useful, it should be noted that if the sensor coils 71, 72, 73 are contained in a plane, the plane need not be perpendicular to the longitudinal axis 61 of the reference coil 60. The angle $\alpha_3$ need not be 90° (see FIG. 4).

The above configurations are possible as fixed configurations for the sensor coil assembly 70 used in the sensor head 90. However, the sensor coil configuration need not be fixed. The sensor coils 71, 72, 73 can be movable and lockable to obtain the best reading of the magnetic field variations. Thus, a sensor coil assembly 70 can have either a plurality of sensor coils with reconfigurable positions relative to each other and relative to the reference coil, or it can have removable sensor coils. Since the reference coil 60 is fixed in relation to the yoke, different sensor coil configurations can be embodied in different installable sensor coil assemblies.

Any suitable means can be used to mount the sensor coils as long as the reference coil 60 is stable and the sensor coils 71, 72, 73 are fixed or locked in their positions.

It should be noted that in performing the measurement of the variations in the magnetic fields, noting the location of the sensor coils 71, 72, 73 relative to the reference coil 60 is crucial. The angles between the axes of the sensor coils relative to the axis of the reference coil must be taken into consideration when mapping the results obtained. This will allow the accurate determination of the depth, angle relative to the surface, and path of any surface defect.

What is claimed is:

1. A sensor head for detecting variations in a magnetic field induced on the surface of a test piece by an electromagnetic elongated yoke, the sensor head comprising:
   a reference coil for sensing magnetic fields produced by the current, the reference coil having a longitudinal axis parallel to a longitudinal axis of the elongated yoke, and the reference coil being disposed between the yoke and the test piece;
   a plurality of sensor coils for sensing variations in magnetic fields, each sensor coil having a longitudinal axis which intersects the longitudinal axis of the reference coil;
   each sensor coil being positioned between the reference coil and the yoke; and
   mounting means for mounting the reference coil and the plurality of sensor coils in the sensor head
   wherein at least one of the plurality of sensor coils has a longitudinal axis not perpendicular to the longitudinal axis of the reference coil.

2. A sensor head as claimed in claim 1 wherein the longitudinal axis of at least one sensor coil is perpendicular to the longitudinal axis of the reference coil.

3. A sensor head as claimed in claim 1 wherein the longitudinal axis of at least one sensor coil is perpendicular to the longitudinal axis of the reference coil, and perpendicular to the surface of the test piece.

4. A sensor head is claimed in claim 1 wherein the plurality of sensor coils comprises three sensor coils.

5. A sensor head as claimed in claim 1 wherein the plurality of sensor coils comprises five sensor coils.

6. A sensor head as claimed in claim 1 wherein an equal number of sensor coils is positioned on each side of a plane containing the longitudinal axes of both the reference coil and the yoke.

7. A sensor head as in claim 1 wherein at least one sensor coil is movable and lockable in place.

8. An ACFM testing module for testing a test piece, the module comprising:
   an electromagnetic elongated yoke;
   a reference coil having a longitudinal axis parallel to a longitudinal axis of the yoke, the reference coil being disposed between the yoke and the test piece;
   three sensor coils, each sensor coil having a longitudinal axis which intersects the longitudinal axis of the reference coil and each sensor coil being positioned between the reference coil and the yoke;
   power supply means providing power to the yoke;
   measurement means coupled separately to the reference coil and to each sensor coil; and
   mounting means for mounting the reference coil and the three sensor coils in a sensor head.

9. An ACFM testing module as claimed in claim 8 wherein at least one of the three sensor coils is movable and lockable in place.

10. A sensor head for use with ACFM crack detection and sizing and for use with an electromagnetic elongated yoke inducing a current sheet in a test piece, the head comprising:
    a reference coil having a longitudinal axis parallel to a longitudinal axis of the yoke, the reference coil being positioned between the test piece and the yoke;
    three sensor coils, each sensor coil having a longitudinal axis at an angle to the longitudinal axis of the reference coil, each sensor coil being positioned between the reference coil and the yoke; and
    mounting means for mounting the reference coil and the three sensor coils in the sensor head;
    wherein the longitudinal axes of the three sensor coils are located in a plane perpendicular to the longitudinal axis of the reference coil.

11. A sensor head as in claim 10 wherein the longitudinal axis of a first sensor coil of the three sensor coils is perpendicular to the longitudinal axis of the reference coil, and perpendicular to a surface of the test piece.

12. A sensor head as in claim 10 wherein at least one of the at least three sensor coils is movable and lockable in place.

13. A method of detecting and sizing defects in or near a surface of a test piece, said method comprising:
    a) energizing a yoke to induce a uniform alternating current on the surface of the test piece
    b) positioning a reference coil such that a longitudinal axis of the reference coil is parallel to a longitudinal axis of the yoke c) positioning at least two sensor coils with their axes at an angle to the reference coil axis at least one sensor coil axis not being perpendicular to the reference coil axis d) moving the sensor head across the surface of the test piece e) detecting variations in electromotive force induced in the reference coil f) measuring the variations detected in step e)

g) detecting variations in electromotive force induced in the sensor coils h) measuring the variations detected in step g)

i) processing data obtained in steps f) and h) to determine a presence and a size of a defect on the surface of the test piece.

14. A method as claimed in claim 13 wherein the sensor head comprises:

a reference coil for sensing magnetic fields produced by the current, the reference coil having a longitudinal axis parallel to a longitudinal axis of the yoke, and the reference coil being disposed between the yoke and the test piece, a plurality of sensor coils for sensing variations in magnetic fields, each sensor coil having a longitudinal axis which intersects the longitudinal axis of the reference coil and each sensor coil being positioned between the reference coil and the yoke, and mounting means for mounting the reference coil and the plurality of sensor coils in the sensor head.

* * * * *